United States Patent
Okada

(10) Patent No.: US 7,125,408 B2
(45) Date of Patent: Oct. 24, 2006

(54) HIGH-FREQUENCY KNIFE

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 276 days.

(21) Appl. No.: 10/777,889

(22) Filed: Feb. 12, 2004

(65) Prior Publication Data

US 2004/0167514 A1    Aug. 26, 2004

(30) Foreign Application Priority Data

Feb. 20, 2003 (JP) .............................. 2003-043110

(51) Int. Cl.
*A61B 18/18* (2006.01)
(52) U.S. Cl. ........................................................ 606/45
(58) Field of Classification Search ................... 606/45, 606/41, 42, 49
See application file for complete search history.

(56) References Cited

U.S. PATENT DOCUMENTS

| 5,846,241 | A  | * | 12/1998 | Kittur et al. ................... 606/48 |
| 6,379,350 | B1 | * | 4/2002  | Sharkey et al. ................ 606/41 |
| 2004/0167514 | A1 | * | 8/2004 | Okada ........................ 606/45 |
| 2004/0210215 | A1 | * | 10/2004 | Okada ........................ 606/45 |
| 2004/0210284 | A1 | * | 10/2004 | Okada ........................ 607/96 |

FOREIGN PATENT DOCUMENTS

JP    4-329944    11/1992

OTHER PUBLICATIONS

T. Oyama et al., "Extended Adaptation of Stomach EMR: Contrivance and Results of Method Aimed at Large En-bloc Resection; Endoscopic Mucosal Resection Using a Hooking Knife", *Stomach and Intestine* 37(9): 1155-1161 (2002).
H. Inoue et al., "Endoscopic Mucosal Resection with a Cap-fitted Panendoscope for Stomach Cancer", *Endoscopia Digestiva, A to Z for How to Select Endoscopic Treatment Tools* 14(9):1301-1302 (2002).

* cited by examiner

*Primary Examiner*—Roy D. Gibson
*Assistant Examiner*—Pete Vrettakos
(74) *Attorney, Agent, or Firm*—Scully, Scott, Murphy & Presser PC

(57) ABSTRACT

A high-frequency knife having a flexible sheath, an operation member, an electrode part, a handled operation section and a connector part. The electrode part is provided with a rod electrode part extending in an axial direction of a flexible sheath, and a plate electrode part. Three corner portions are provided on an external peripheral portion of the plate electrode part.

7 Claims, 5 Drawing Sheets

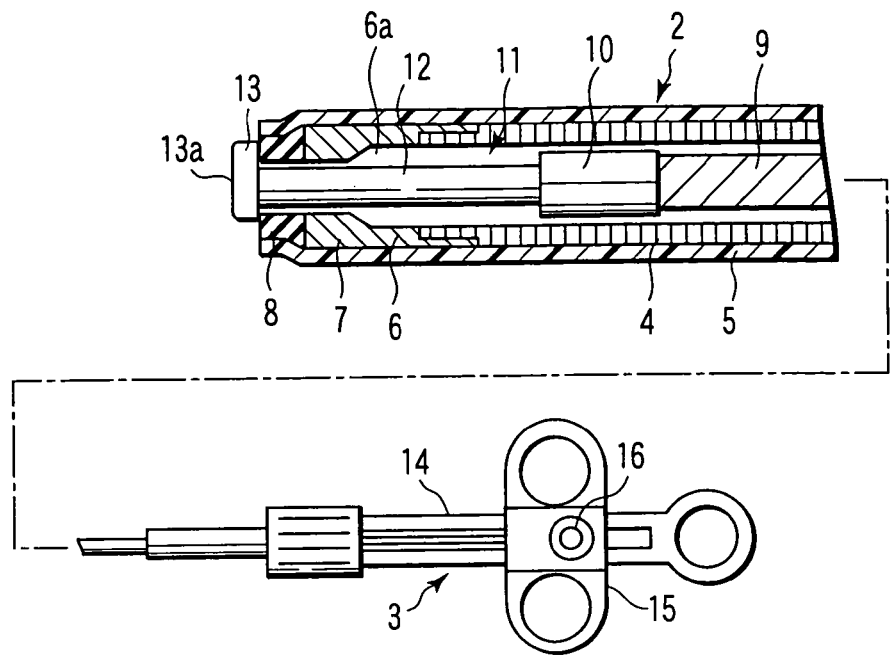
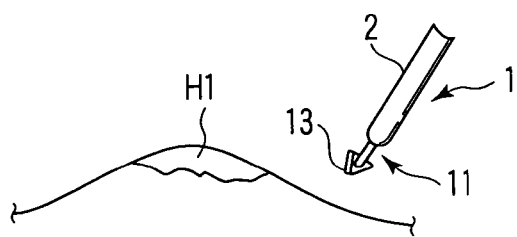
FIG. 3
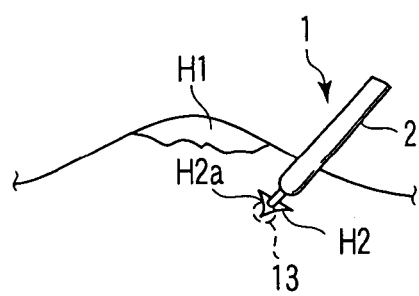
FIG. 4A
FIG. 4B
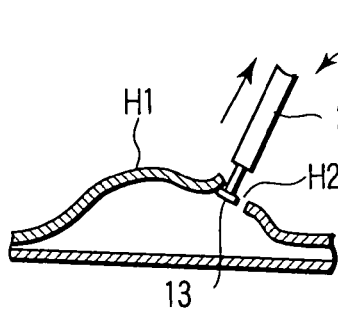
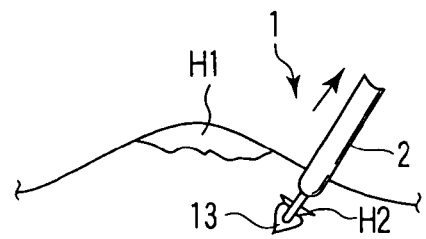
FIG. 4C
FIG. 4D

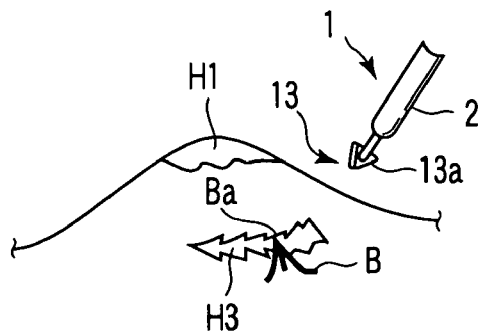
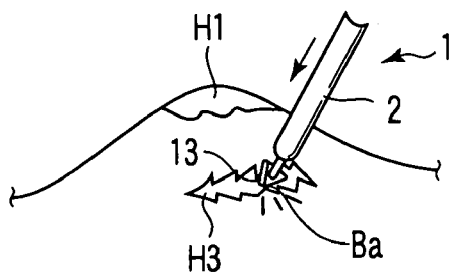
FIG. 5A
FIG. 5B
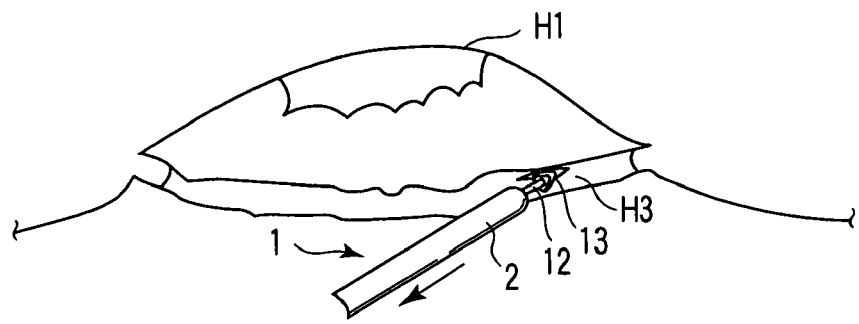
FIG. 6
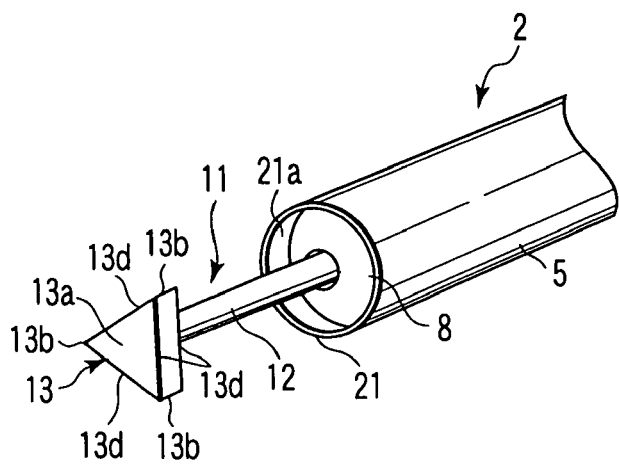
FIG. 7A
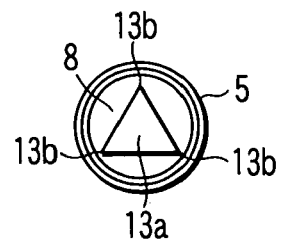
FIG. 7B

HIGH-FREQUENCY KNIFE

CROSS-REFERENCE TO RELATED APPLICATIONS

This application is based upon and claims the benefit of priority from the prior Japanese Patent Application No. 2003-043110, filed Feb. 20, 2003, the entire contents of which are incorporated herein by reference.

BACKGROUND OF THE INVENTION

1. Field of the Invention

The present invention relates to a high-frequency knife (diathermic cutter) for excising a living tissue by high-frequency incision.

2. Description of the Related Art

There have been performed treatments in which a treatment instrument for incision is inserted in the body through, for example, a channel of an endoscope, and a living tissue such as a mucous membrane in the body is excised by the treatment instrument. A high-frequency treatment instrument (diathermic accessories) as disclosed in Jpn. Pat. Appln. KOKAI Pub. No. 4-329944 (Patent Document 1) is used for such an excision treatment.

The high-frequency treatment instrument disclosed in Patent Document 1 has an elongated inserting section, and a handheld operating section which is located on the side closer to the operator's hand and connected to a proximal end portion of the inserting section. The inserting section is inserted in the body through a channel of an endoscope. The inserting section has an elongated flexible tube having flexibility, and an operation wire which is axially-movably inserted into the flexible tube. The operating section has an operation handle. The operation wire is axially moved back and forth in synchronization with the operation of the operation handle. A needle-shaped knife section (electrode section) extending in the axial direction is provided on a distal end portion of the operation wire.

When the operation handle is operated, the operation wire is moved in the axial direction. By moving the operation wire, the knife section is projected from and retracted into the flexible tube. In this operation, the knife section is moved between a retracted position, where the knife section is housed in the flexible tube, and a use position where the knife section is projected outside the flexible tube. A living tissue contacting the knife section is cauterized and incised by the passage of a high-frequency current through the knife section, in the state where the knife section has been moved to the use position.

As a publicly-known non-patent document, there is Non-patent Document 1: Tuneo Oyama, et al., "Extended Adaptation of Stomach EMR: Contrivance and Results of Method Aimed at Large En-bloc Resection; Endoscopic Mucosal Resection Using a Hooking Knife", Stomach and Intestine, August 2002, Vol. 37, No. 9, pp. 1155–1161. The Non-patent Document 1 discloses a high-frequency treatment instrument having a structure different from that disclosed in Patent Document 1. The high-frequency treatment instrument has a bent portion made by bending a distal end of its needle-shaped knife section (electrode section). In use of the high-frequency treatment instrument, a living tissue is hooked onto the bent portion of the knife section, and cauterized and incised while being pulled up by the bent portion.

As another publicly-known non-patent document, there is Non-patent Document 2: Haruhiro Inoue et al., "Endoscopic Mucosal Resection with a Cap-fitted Panendoscope for Stomach Cancer", Endoscopia Digestiva, A to Z for How to Select Endoscopic Treatment Tools, September 2002, Vol. 14, No. 9, pp. 1301–1302. The Non-patent Document 2 discloses a high-frequency treatment instrument having another structure. The high-frequency treatment instrument has a disc-shaped electrode portion at a distal end of a needle-shaped knife section (electrode section). In use of the high-frequency treatment instrument, a living tissue is hooked onto the disk-shaped electrode portion of the knife section, and cauterized and incised while being pulled up by the disk-shaped electrode portion. Further, the disk-shaped electrode portion is pressed against a bleeding region, and thereby provides hemostasis to the bleeding region by coagulation.

If a living tissue is excised by using the high-frequency treatment instrument of the Patent Document 1, the knife section is stuck into a region to be excised, and then moved in a predetermined excision direction in the stuck state.

The following is an operation of excising a living tissue by using the high-frequency treatment instrument of Non-patent Document 1 or 2. The distal end of the knife section is inserted in a living tissue and pulled up, and thereby the living tissue is hooked onto the bent portion or the disk-shaped portion. This prevents the stuck knife portion from contacting a not-to-be-excised region.

BRIEF SUMMARY OF THE INVENTION

The present invention provides a high-frequency knife, comprising:

an electrically insulating flexible sheath having a distal end and a proximal end;

an operation member having a distal end and a proximal end, and movable in an axial direction in the sheath;

an electrode part provided on the distal end of the operation member, at least a part of the electrode part being axially projected from and retracted in the distal end of the sheath, the electrode part having a rod electrode part extending in the axial direction of the sheath and a plate electrode part disposed on a distal end of the rod electrode part, the plate electrode part including a plane surface part extending in a direction crossing the axis direction of the sheath, a handheld operation section provided on the proximal end of the sheath, the operation section having a slider part which moves the operation member in the axial direction of the sheath; and a connector part provided on the slider part, and having an internal end portion and an external end portion, the external end portion being electrically connected with a cord communicating with a high-frequency generating source, and the internal end portion being electrically connected with the electrode part through the operation member.

The plate electrode part preferably has a plurality of hook portions on its external periphery.

The plate electrode part preferably has a disc, and the hook portions are a plurality of projections provided on an external peripheral surface of the disc, and the projections are arranged along a line in a peripheral direction on the external peripheral surface of the disc.

The plate electrode part preferably has a polygonal plate.

The polygonal plate preferably has a triangular shape, and the hook portions are corner portions of the triangular plate.

The corner portions has preferably sharp edge.

The plate electrode part preferably has a plurality of rod arms projected outward from a central portion of the plate electrode part, and the arms are connected to each other to form a polygonal shape.

The sheath preferably has at its distal end a receiving part for the plate electrode part.

Advantages of the invention will be set forth in the description which follows, an in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a cross-sectional side view of a main part of the high-frequency knife according to the first embodiment, in the state where the knife section is retracted into the sheath.

FIG. 4A is a perspective view illustrating the state where the distal end portion of the high-frequency knife according to the first embodiment is brought close to a diseased mucous membrane part to be excised in a body cavity.

FIG. 4B is a perspective view illustrating the state where a first incision is performed to bore a hole in a mucous membrane around the diseased mucous membrane part.

FIG. 4C is a vertical cross-sectional view of a main part of the mucous membrane hooked onto and pulled up by a plate electrode section.

FIG. 4D is a perspective view illustrating incision of the diseased mucous membrane part by the knife section.

FIG. 5A is a perspective view illustrating the state where an incised region bleeds in incision during use of the high-frequency knife of the first embodiment.

FIG. 5B is a perspective view illustrating an operation of hemostasis by coagulating the bleeding point.

FIG. 6 is a perspective view illustrating an operation wherein the knife section is brought into contact with an incision made by incising a part around the diseased mucous membrane part by the high-frequency knife of the first embodiment, and the diseased mucous membrane part is separated by successive incision.

FIG. 7A is a perspective view illustrating a distal end portion of a high-frequency knife according to a second embodiment of the present invention.

FIG. 7B is a front view of a knife section of the second embodiment.

DETAILED DESCRIPTION OF THE INVENTION

Figure 1A:
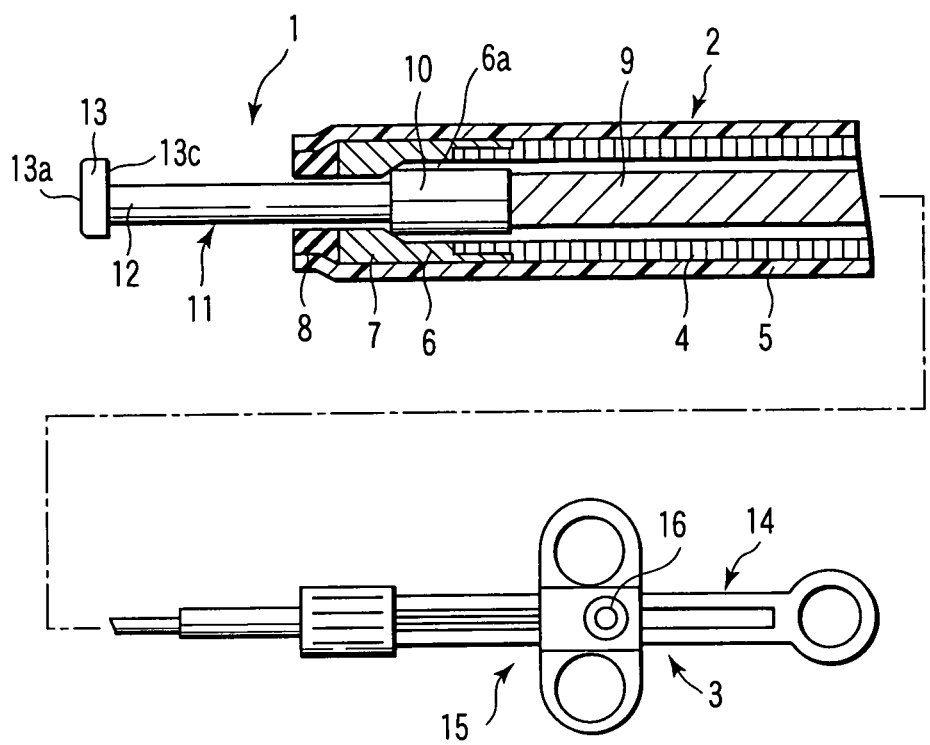
FIG. 1A is a cross-sectional side view of a main part of a high-frequency knife according to a first embodiment of the present invention, in the state where a knife section is projected from a sheath.

A first embodiment of the present invention will now be explained with reference to FIGS. 1A to 6. FIG. 1A illustrates a schematic structure of a high-frequency knife 1 of the first embodiment. The high-frequency knife 1 comprises an elongated flexible sheath 2, and an operation section 3 provided on a proximal end of the sheath 2. The sheath 2 can be inserted into a channel of an endoscope (not shown). The sheath 2 is formed of, for example, a close-wound coil 4, and an insulating tube 5 which covers the external periphery of the close-wound coil 4. The insulating tube 5 is made of, for example, a tetrafluoroethylene material. A proximal end of a tube-shaped stopper member 6 is connected to a distal end of the close-wound coil 4, in the state of being fitted onto the close-wound coil 4. The stopper member 6 is connected such that the external periphery of the stopper member 6 is aligned with the external peripheral surface of the close-wound coil 4 on the same plane, with no difference in level. The external periphery of the stopper member 6 is covered with the distal end portion of the insulating tube 5.

Further, at the internal peripheral surface of the stopper member 6, there are formed a thick wall portion 7 projecting inward and located on the distal end side, and a large-diameter hole portion 6a having a thin wall thickness and located behind the thick wall portion 7. The thick wall portion 7 makes the thickness on the distal end side of the stopper member 6 greater in the radial internal direction than the thickness of the large-diameter hole portion 6a on the proximal end side of the stopper member 6.

A ring-shaped sheath end insulating chip 8 is provided on the distal end side of the thick wall portion 7. The internal periphery of the sheath end insulating chip 8 is formed to be almost aligned with the internal peripheral surface of the thick wall portion 7. The external periphery of the sheath end insulating chip 8 is covered with the insulating tube 5.

A conductive operation wire 9 is axially movably inserted through the sheath 2. A conductive stopper receiving part 10 is mounted on the distal end of the operation wire 9. The stopper receiving part 10 is inserted into the large-diameter hole portion 6a of the stopper member 6, and in contact with the thick wall portion 7.

Figure 2:
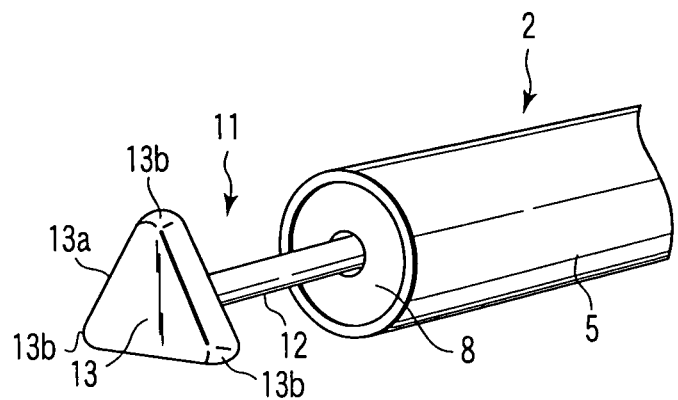
FIG. 2 is a perspective view illustrating a distal end portion of the high-frequency knife of the first embodiment.

Further, a knife section (electrode section) 11 shown in FIG. 2 is connected to the stopper receiving part 10 on the distal end of the operation wire 9. The knife section 11 has a rod electrode part 12, and a plate electrode part 13 provided on the distal end of the rod electrode part 12. The rod electrode part 12 projects from the distal end of the sheath 2 in its axial direction. The plate electrode 13 includes a plane surface portion extending in a direction crossing the extending direction of the rod electrode part 12. The rod electrode part 12 is made of a conductive material. The proximal end of the rod electrode 12 is electrically connected to the stopper receiving part 10.

Figure 1B:
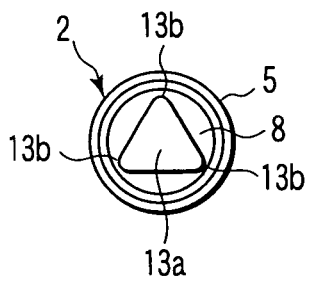
FIG. 1B is a front view of the knife section.

The plate electrode part 13 is made of a conductive material which is formed as unitary one piece with the distal end of the rod electrode part 12. As shown in FIG. 1B, the plate electrode part 13 has a triangular tip plane surface portion 13a included in a plane which is generally vertical to the axis of the rod electrode part 12, and three rounded corner portions (hook portions) 13b.

The operation section 3 of the high-frequency knife 1 comprises an operation section main body 14 having a shaft shape, and an operation slider 15 which is axially slidable with respect to the operation section main body 14. A connector part 16 is projectingly provided on the operation slider 15. The connector part 16 is electrically connected with a code (not shown) communicating with a high-frequency generator (not shown).

Further, the operation section main body 14 is provided with an inserting hole (not shown) through which the operation wire 9 is inserted. The proximal end portion of the operation wire 9 passes through the inserting hole of the operation section main body 14, extends rearward, and is connected to the operation slider 15.

When the operation slider 15 is axially slid, the operation wire 9 axially moves back and forth in the internal hole of the sheath 2. The back-and-forth movement of the operation wire 9 projects and retracts the rod electrode part 12 of the knife section 11 from, or into, the distal end portion of the sheath 2.

The proximal end portion of the operation wire 9 is electrically connected to the connector part 16. Thereby, the plate electrode part 13 of the knife section 11 is electrically connected to the connector part 16 of the operation slider 15, through the rod electrode part 12, the stopper receiving part 10 and the operation wire 9.

Next, an operation of the high-frequency knife 1 of this embodiment, having the above structure, will now be explained. First, the use of the high-frequency knife 1 will be explained. In use of the high-frequency knife 1, the operation slider 15 and the operation section main body 14 of the operation section 3 are held. Then, when the operation slider 15 is moved backward (to the proximal end) with respect to the operation section main body 14, the operation wire 9 is moved backward. Simultaneously with the movement, the rod electrode part 12 is retracted into the sheath 2, as shown in FIG. 3. In retraction, the proximal end surface 13c of the plate electrode part 13 is brought into contact with the insulating chip 8 at the distal end of the sheath 2. The knife section 11 is mainly is maintained in this state, when the knife section 11 is not used, such as when the knife is inserted into the channel of an endoscope.

When the operation slider 15 is moved forward (to the distal end) with respect to the operation section main body 14, the operation wire 9 is moved forward. Simultaneously with the movement, as shown in FIG. 1A, the rod electrode part 12 is projected outward from the distal end of the sheath 2, and moved to a position where the proximal end surface 13c of the plate electrode part 13 is moved forward and separated from the distal end of the sheath 2. The knife is used in this state, when the knife section 11 is energized and used for excising the mucous membrane.

Next, the operation of the high-frequency knife 1 in excision of mucous membrane in a body cavity by inserting the high-frequency knife 1 in the body through a channel of an endoscope and the like will now be explained, with reference to FIGS. 4A to 6. First, a syringe needle (not shown) is introduced into a body cavity through a channel of an endoscope (not shown). Then, as shown in FIG. 4A, physiological saline solution is injected from the syringe needle into a lower layer of mucous membrane including a diseased mucous membrane part H1 which is the part to be excised in the body cavity, to raise (swell, bulge) the diseased mucous membrane part H1.

Then, an antipole plate (patient plate) (not shown) is fitted on a patient. Thereafter, the high-frequency knife 1 in the state where the knife section 11 has been retracted into the sheath 2 is introduced into the body cavity also through the channel of the endoscope. Then, the sheath 2 of the high-frequency knife 1 is projected from the channel of the endoscope, and the knife section 11 of the high-frequency knife 1 is projected from the distal end of the sheath 2, as shown in FIG. 4A. Thereafter, first incision is performed to bore a hole H2 in the mucous membrane around the diseased mucous membrane part H1, as shown in FIG. 4B.

Then, as shown in FIG. 4C, a part of a rim portion H2a of the hole H2 is hooked onto the plate electrode part 13, and the knife section 11 is moved in the axial direction of the rod electrode part 12 (vertical direction) to pull up the mucous membrane. In this state, a high-frequency current is supplied to the knife section 11. Thereby, the mucous membrane pulled up by the plate electrode part 13 is incised by the proximal end surface 13c of the plate electrode part 13, as shown in FIG. 4D. By repeating this operation, all the part surrounding the diseased mucous membrane part H1 is incised.

Further, as shown in FIG. 5A, if bleed B from the incised region occurs during incision, the tip plane surface portion 13a of the plate electrode part 13 of the high-frequency knife 1 is pressed against a bleeding point Ba and energized, as shown in FIG. 5B. Thereby, the bleeding point Ba is coagulated and the bleeding is stopped.

As described above, the diseased mucous membrane part H1 is completely incised through the peripheral direction. Thereafter, as shown in FIG. 6, the knife section 11 is brought into contact with an incision H3 obtained by incising the part surrounding the diseased mucous membrane part H1. In this state, in the same manner as the incision in the peripheral direction, the diseased mucous membrane part H1 is hooked onto and pulled up by the plate electrode part 13, and sequentially incised and separated. Thereby, the diseased mucous membrane part H1 is completely excised. Thereafter, the excised diseased mucous membrane part H1 is held by forceps (not shown) and the like, and taken out of the body through the channel of the endoscope, and thereby the treatment is ended.

The above structure produces the following effects. In the high-frequency knife 1 according to this embodiment, the knife section 11 is formed by the rod electrode part 12 and the plate electrode part 13. The plate electrode part 13 is provided with the plane portion 13a which is generally vertical to the axis of the rod electrode part 12, and the three corner portions 13b serving as plural hook portions are provided on the external periphery of the plane portion 13a. Since a living tissue is hooked onto any one of the three corner portions 13b of the plate electrode part 13, it is unnecessary to adjust the orientation of the knife section 11, onto which the living tissue is to be hooked, in agreement with the incision region, and the living tissue is sufficiently hooked.

Further, the tip plane surface portion 13a of the plate electrode part 13 can stop bleeding by coagulation, it is possible to rapidly provide hemostasis to the bleeding B during operation.

Figure 8:
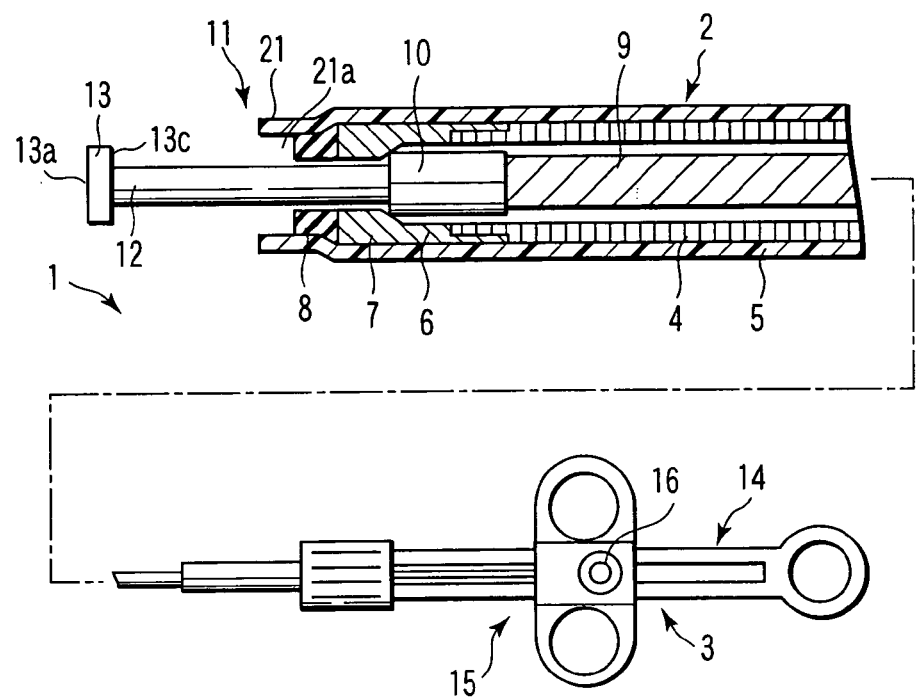
FIG. 8 is a cross-sectional side view of a main part the knife section of the high-frequency knife according to the second embodiment, in the projection state where the knife section is projected from a sheath.
Figure 9:
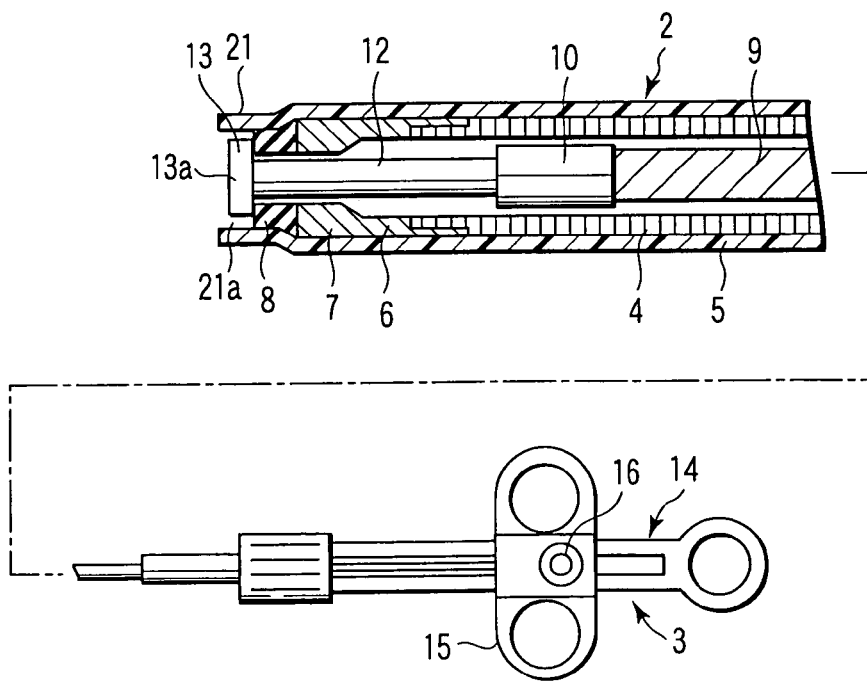
FIG. 9 is a cross-sectional side view of a main part of the knife section of the high-frequency knife according to the second embodiment, in the retraction state where the knife section is retracted into the sheath.

FIGS. 7 to 9 illustrate a second embodiment of the present invention. This embodiment is obtained by changing the structure of the high-frequency knife 1 of the first embodiment (please refer to FIGS. 1A to 6) as follows. The other parts of the second embodiment have the same constitutions as those in the high-frequency knife of the first embodiment. The same parts as those in the high-frequency knife 1 of the first embodiment are denoted by the same reference numerals, and their explanations are omitted.

Specifically, in a high-frequency knife 1 of this embodiment, corner portions 13b and edge portions 13d of a plate electrode part 13 are formed with sharp edges, as shown in FIGS. 7A and 7B.

As shown in FIG. 8, a distal end extension part 21 extending over the distal end of an insulating chip 8 is provided on the distal end portion of an insulating tube 5 of a sheath 2. The distal end extension part 21 forms a receiving part 21a for the plate electrode part 13, as shown in FIG. 9.

Next, the operation of the high-frequency knife 1 of this embodiment will now be explained. Explanations of the same operations as in the first embodiment will be omitted. In use of the high-frequency knife 1 of the second embodiment, when an operation slider 15 of an operation section 3 is moved backward (to the proximal end) with respect to an operation section main body 14, an operation wire 9 is moved backward. In this operation, in the second embodiment, a rod electrode part 12 is retracted into the sheath 2, a proximal end surface 13c of the plate electrode part 13 is brought into contact with the insulating chip 8 of the sheath 2, and the plate electrode part 13 is received in the receiving part 21a at the distal end of the sheath 2, as shown in FIG. 9. The other operations of the second embodiment are the same as those in the first embodiment.

The second embodiment produces the following effects. In the high-frequency knife 1 of the second embodiment, when the mucous membrane is incised in the state of being hooked onto the plate electrode part 13 and pulled up thereby, the mucous membrane is more securely hooked by the edge portions of the corner portions 13b and the edge portions 13d of the plate electrode part 13. Further, when the rod electrode part 12 is retracted into the sheath 2 and the proximal end surface 13c of the plate electrode part 13 is brought into contact with the insulating chip 8 of the sheath 2, the plate electrode part 13 is received in the receiving part 21a inside the distal end extension part 21. Therefore, the plate electrode part 13 is not kept exposed to the outside, thus the edges of the plate electrode part 13 do not damage the channel of the endoscope when it is inserted into the channel.

Figure 10:
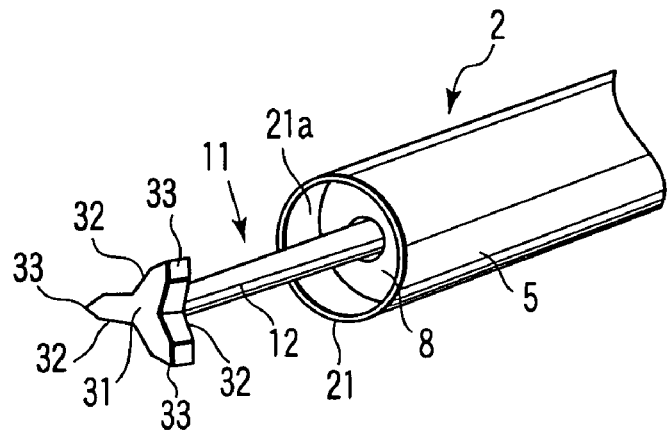
FIG. 10 is a perspective view of a main part of a third embodiment of the present invention.

FIG. 10 illustrates a third embodiment of the present invention. This embodiment is made by changing the structure of the knife section 11 of the high-frequency knife 1 according to the second embodiment (please refer to FIGS. 7A to 9) as follows.

Specifically, in a knife section 11 of a high-frequency knife 1 of the third embodiment, the form of the plate electrode part 13 has been changed as follows. A plate electrode part 31 of the third embodiment has three arm-shaped projecting portions 32. The three projecting portions 32 are projected outward from the central portion of the plate electrode part 31. Each of the projecting portions 32 is formed in a tapering shape tapering toward its distal end. Further, a sharp corner portion 33 having a nearly angle shape is formed on the distal end of each of the projecting portions 32.

In use of the high-frequency knife 1 of the third embodiment, in the same manner as in the second embodiment, when an operation slider 15 of an operation section 3 is moved backward (to the proximal end) with respect to an operation section main body 14, an operation wire 9 is moved backward. In this operation, in the third embodiment, a rod electrode part 12 is retracted into a sheath 2, the rear surface of the plate electrode part 31 is brought into contact with an insulating chip 8 of the sheath 2, and the plate electrode part 31 is received in a receiving part 21a at the distal end of the sheath 2.

The above structure produces the following effects. In the high-frequency knife 1 of the third embodiment, when the rod electrode part 12 is retracted into the sheath 2, the plate electrode part 31 is received in the receiving part 21a inside a distal end extension part 21. Therefore, in the same manner as the second embodiment, it produces the effect that the edges of the plate electrode part 31 do not damage the channel of an endoscope, when it is inserted into the channel.

Further, in particular, in the third embodiment, the three arm-shaped projecting portions 32 are projected outward from the central portion of the plate electrode part 31. Each of the projecting portions 32 has a shape tapering toward its distal end, and a sharp corner portion 33 having a generally angle shape is formed on the distal end of each projecting portion 32. This produces the effect that a living tissue is more securely hooked, when the mucous membrane is incised in the state of being hooked onto and pulled up by the plate electrode part 31.

Figure 11:
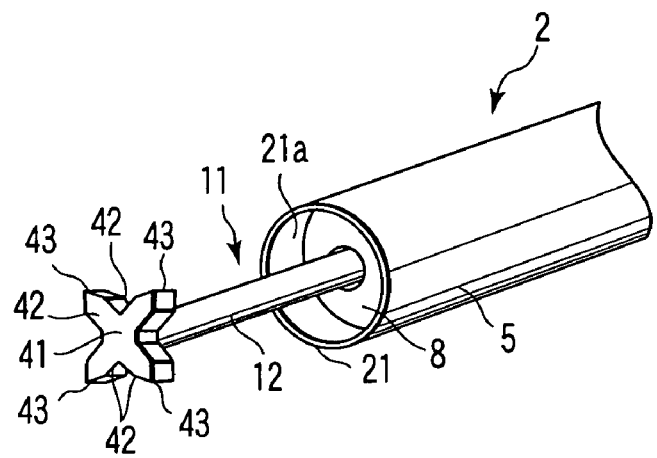
FIG. 11 is a perspective view of a main part of a fourth embodiment of the present invention.

FIG. 11 illustrates a fourth embodiment of the present invention. This embodiment is obtained by further changing the structure of the plate electrode part 13 in the knife section 11 of the high-frequency knife 1 in the second embodiment (please refer to FIGS. 7A to 9) as follows.

Specifically, a plate electrode part 41 of a knife section 11 of a high-frequency knife 1 according to the fourth embodiment is formed to have a cross shape crossing at nearly right angles. The cross-shaped plate electrode part 41 has four arm-shaped projecting portions 42. The four projecting portions 42 are projected outward from the central portion. A sharp corner portion 43 having a generally angle shape is formed on the distal end of each projecting portion 42.

Further, in use of the high-frequency knife 1 of the fourth embodiment, in the same manner as in the second and third embodiments, when an operation slider 15 of an operation section 3 is moved backward (to the proximal end) with respect to an operation section main body 14, an operation wire 9 is moved backward. In this operation, in the fourth embodiment, a rod electrode part 12 is retracted-into a sheath 2, the rear surface of the plate electrode part 41 is brought into contact with an insulating chip 8 of the sheath 2, and the plate electrode part 41 is received in a receiving part 21a on the distal end of the sheath 2.

The above structure produces the following effects. In the high-frequency knife 1 of the fourth embodiment, when the rod electrode part 12 is retracted into the sheath 2, the plate electrode part 41 is received in the receiving part 21a inside a distal end extension part 21. Therefore, in the same manner as the second and third embodiments, it produces the effect that the edges of the plate electrode part 41 do not damage the channel of an endoscope when it is inserted into the channel.

Further, in particular, in the fourth embodiment, the four projecting portions 42 are projected outward from the central portion of the plate electrode part 41, and a sharp corner portion 43 having a generally angle shape is formed on the distal end portion of each projecting portion 42. Therefore, the fourth embodiment has the corner portions 43 greater in number than those in the third embodiment, thus produces the effect of further simplifying adjustment of the orientation of the plate electrode part 41.

Figure 12:
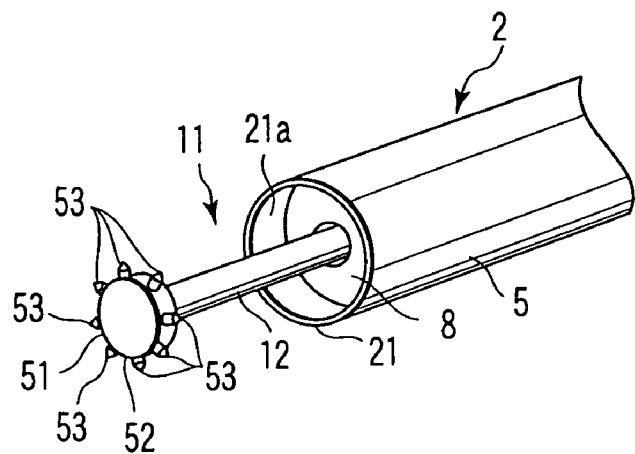
FIG. 12 is a perspective view of a main part of a fifth embodiment of the present invention.

FIG. 12 illustrates a fifth embodiment of the present invention. This embodiment is obtained by further changing the structure of the plate electrode part 13 in the knife section 11 of the high-frequency knife 1 according to the second embodiment (please refer to FIGS. 7A to 9) as follows.

Specifically, in a plate electrode part 51 in a knife section 11 of a high-frequency knife 1 of the fifth embodiment, a plurality of sharp projections 53 are formed on the external peripheral surface of a disc 52. The projections 53 are arranged along a line in the peripheral direction on the external peripheral surface of the disc 52.

In use of the high-frequency knife 1 of the fifth embodiment, in the same manner as in the second to fourth embodiments, when an operation slider 15 of an operation section 3 is moved backward (to the proximal end) with respect to an operation section main body 14, an operation wire 9 is moved backward. In this operation, in the fifth embodiment, a rod electrode part 12 is retracted into a sheath 2, the rear surface of the plate electrode part 51 is brought into contact with an insulating chip 8 of the sheath 2, and the plate electrode part 51 is received in a receiving part 21a on the distal end of the sheath 2.

The above structure produces the following effects. In the high-frequency knife 1 of the fifth embodiment, when the rod electrode part 12 is retracted into the sheath 2, the plate electrode part 51 is received in the receiving part 21a inside a distal end extension part 21. As a result, in the same manner as the second to fourth embodiments, it produces the effect that the edges of the plate electrode part 51 do not damage the channel of an endoscope when it is inserted into the channel.

Further, in particular, in the fifth embodiment, the plate electrode part 51 of the knife section 11 have the structure where plural sharp projections 53 are provided on the peripheral surface of the disc 52, and the projections 53 are arranged along a line in the peripheral direction on the peripheral surface of the disc 52. Therefore, like the fourth embodiment, the fifth embodiment produces the effect of further simplifying adjustment of the orientation of the plate electrode part 51.

Additional advantages and modifications will readily occur to those skilled in the art. Therefore, the invention in its broader aspects is not limited to the specific detailed and representative embodiments shown and described herein. Accordingly, various modifications may be made without departing from the spirit or scope of the general inventive concept as defined by the appended claims and their equivalents.

What is claimed is:

1. A high-frequency knife, comprising:
an electrically insulating flexible sheath having a distal end and a proximal end;
an operation member inserted into the sheath to be movable in an axial direction therein;
an operation section provided on the proximal end of the sheath, the operation section having a slider part which moves the operation member in the axial direction of the sheath; and
an electrode part provided on the distal end of the operation member, at least a part of the electrode part being axially projected from and retracted in the distal end of the sheath, the electrode part having a rod electrode part extending in the axial direction of the sheath and a plate electrode disposed on a distal end of the rod electrode part, the plate electrode part including a plane surface part extending in a direction crossing the axis direction of the sheath; and
a plurality of electro-conductive projecting portions formed on the plate electrode part and projecting in an extending direction of a plane surface of the plate electrode part, the plurality of electro-conductive projecting portions projecting in directions different from each other.

2. A high-frequency knife according to claim 1, wherein the plate electrode part has a disc, and
hook portions having a plurality of projections provided on an external peripheral surface of the disc, the projections being arranged along a line in a peripheral direction on the external peripheral surface of the disc.

3. A high-frequency knife according to claim 1, wherein the plate electrode part has a polygonal plate.

4. A high-frequency knife according to claim 3, wherein the polygonal plate has a triangular shape, and hook portions that are provided on corner portions of the triangular plate.

5. A high-frequency knife according to claim 4, wherein the corner portions has sharp edge.

6. A high-frequency knife according to claim 2, wherein the plate electrode part has a plurality of rod arms projected outward from a central portion of the plate electrode part, and the arms being connected to each other to form a polygonal shape.

7. A high-frequency knife according to claim 1, wherein the sheath has at its distal end a receiving part for the plate electrode part.

* * * * *